(12) United States Patent
Angold et al.

(10) Patent No.: US 9,782,892 B2
(45) Date of Patent: Oct. 10, 2017

(54) EXOSKELETON AND METHOD OF INCREASING THE FLEXIBILITY OF AN EXOSKELETON JOINT

(71) Applicant: Ekso Bionics, Inc., Richmond, CA (US)

(72) Inventors: Russdon Angold, American Canyon, CA (US); Adam Preuss, Santa Rose, CA (US); Nicholas Fleming, San Francisco, CA (US); Matthew D Sweeney, Sacramento, CA (US)

(73) Assignee: Ekso Bionics, Inc., Richmond, CA (US)

(*) Notice: Subject to any disclaimer, the term of this patent is extended or adjusted under 35 U.S.C. 154(b) by 0 days.

(21) Appl. No.: 15/023,773

(22) PCT Filed: Apr. 24, 2015

(86) PCT No.: PCT/US2015/027523
§ 371 (c)(1),
(2) Date: Mar. 22, 2016

(87) PCT Pub. No.: WO2015/187258
PCT Pub. Date: Dec. 10, 2015

(65) Prior Publication Data
US 2016/0229049 A1 Aug. 11, 2016

Related U.S. Application Data

(60) Provisional application No. 61/987,696, filed on May 2, 2014.

(51) Int. Cl.
*A61H 3/00* (2006.01)
*B25J 9/00* (2006.01)
*F16M 13/04* (2006.01)
*A61F 5/01* (2006.01)
*A61F 2/60* (2006.01)

(52) U.S. Cl.
CPC ............... *B25J 9/0006* (2013.01); *A61F 2/60* (2013.01); *A61F 5/0111* (2013.01); *A61H 3/00* (2013.01); *F16M 13/04* (2013.01)

(58) Field of Classification Search
CPC .. A61H 1/02; A61H 1/0262; A61H 3/00; B25J 9/0006; A61F 5/0111
USPC ...................................... 602/16–30
See application file for complete search history.

(56) References Cited

U.S. PATENT DOCUMENTS

| | | | | |
|---|---|---|---|---|
| 406,328 A | * | 7/1889 | Yagn | A63B 25/10 297/4 |
| 1,354,427 A | * | 9/1920 | Welter | A61F 5/0113 602/27 |
| 1,407,369 A | | 2/1922 | Beurdeley | |
| 2,573,866 A | | 11/1951 | Murphy | |
| 2,712,310 A | * | 7/1955 | Giambra | A61F 5/0113 602/28 |

(Continued)

*Primary Examiner* — Justine Yu
*Assistant Examiner* — Christopher Miller
(74) *Attorney, Agent, or Firm* — Diederiks & Whitelaw, PLC

(57) ABSTRACT

An exoskeleton configured to be coupled to a user includes a plurality of interconnected support elements constituted by rigid compression members interconnected through a tensegrity joint. The joint includes a tensile member having a first end and a second end coupled to first and second ones of the support elements respectively.

20 Claims, 13 Drawing Sheets

(56) References Cited

U.S. PATENT DOCUMENTS

| | | | |
|---|---|---|---|
| 2,949,111 A * | 8/1960 | Ruotoistenmaki | A61F 5/0113 602/28 |
| 3,589,359 A * | 6/1971 | Hill | A61F 5/0113 602/28 |
| 3,928,872 A * | 12/1975 | Johnson | A61F 5/0106 2/22 |
| 4,408,600 A * | 10/1983 | Davis | A61F 5/0106 2/22 |
| 4,456,003 A * | 6/1984 | Allard | A61F 5/0102 602/16 |
| 4,531,515 A | 7/1985 | Rolfes | |
| 4,649,906 A * | 3/1987 | Spademan | A61F 5/0125 602/26 |
| RE32,650 E * | 4/1988 | Waddell | A61F 5/0106 2/22 |
| 5,020,790 A | 6/1991 | Beard et al. | |
| 5,038,764 A * | 8/1991 | Paez | A61F 5/0118 602/22 |
| 5,058,574 A * | 10/1991 | Anderson | A61F 5/0125 602/16 |
| 5,117,814 A * | 6/1992 | Luttrell | A61F 5/0123 601/33 |
| 5,286,251 A * | 2/1994 | Thompson | A61F 5/3715 128/100.1 |
| 5,362,288 A * | 11/1994 | Razon | A63B 69/0028 482/51 |
| 5,653,467 A * | 8/1997 | Griffin | A63C 11/001 280/809 |
| 6,090,057 A * | 7/2000 | Collins | A61F 5/0193 602/16 |
| 7,553,266 B2 * | 6/2009 | Abdoli-Eramaki | A61F 5/026 482/124 |
| 7,766,851 B2 * | 8/2010 | Lindh | A61F 5/0113 602/16 |
| 8,060,945 B2 | 11/2011 | Adarraga | |
| 8,235,924 B2 | 8/2012 | Bachmann et al. | |
| 8,323,224 B2 * | 12/2012 | Shlomovitz | A61F 5/0111 602/23 |
| 8,356,448 B2 | 1/2013 | Nihei | |
| 8,480,760 B2 | 7/2013 | Hansen et al. | |
| 8,585,626 B2 * | 11/2013 | Cerioli | A61F 5/0111 602/23 |
| 8,597,369 B2 | 12/2013 | Hansen et al. | |
| 8,702,632 B2 | 4/2014 | Han et al. | |
| 8,740,822 B2 | 6/2014 | Hiki et al. | |
| 8,790,282 B2 | 7/2014 | Jung et al. | |
| 8,821,589 B2 | 9/2014 | Rifkin | |
| 9,539,466 B1 * | 1/2017 | Schoner | A63B 23/0476 |
| 2002/0082711 A1 | 6/2002 | Kuhn et al. | |
| 2003/0030397 A1 * | 2/2003 | Simmons | B25J 9/0006 318/568.11 |
| 2003/0120183 A1 * | 6/2003 | Simmons | A61F 4/00 600/595 |
| 2005/0059908 A1 | 3/2005 | Bogert | |
| 2005/0216097 A1 * | 9/2005 | Rifkin | A61F 2/60 623/53 |
| 2007/0004570 A1 | 1/2007 | Afanasenko et al. | |
| 2007/0027419 A1 * | 2/2007 | Drennan | A61F 5/0193 602/19 |
| 2007/0100268 A1 * | 5/2007 | Fisher | A61F 5/0113 602/28 |
| 2007/0123997 A1 | 5/2007 | Herr et al. | |
| 2008/0300525 A1 * | 12/2008 | Shlomovitz | A61F 5/0111 602/28 |
| 2009/0292369 A1 | 11/2009 | Kazerooni et al. | |
| 2010/0286796 A1 | 11/2010 | Clausen | |
| 2011/0015762 A1 * | 1/2011 | Rifkin | A61F 2/66 623/53 |
| 2011/0054634 A1 | 3/2011 | Bartlett | |
| 2011/0066088 A1 | 3/2011 | Little et al. | |
| 2011/0160630 A1 * | 6/2011 | Cerioli | A61F 5/0111 602/23 |
| 2011/0208322 A1 * | 8/2011 | Rifkin | A61F 2/66 623/55 |
| 2012/0271207 A1 | 10/2012 | Schoen et al. | |
| 2013/0046218 A1 | 2/2013 | Wiggin et al. | |
| 2013/0079686 A1 * | 3/2013 | Sessions | A61H 1/0266 601/27 |
| 2013/0226048 A1 | 8/2013 | Unluhisarcikli et al. | |
| 2013/0245524 A1 | 9/2013 | Schofield | |
| 2013/0296746 A1 | 11/2013 | Herr et al. | |
| 2014/0012173 A1 * | 1/2014 | Newman | A61F 5/0127 602/28 |
| 2014/0088728 A1 | 3/2014 | Herr | |
| 2014/0090677 A1 | 4/2014 | Butler | |
| 2014/0148738 A1 | 5/2014 | Nagasaka et al. | |
| 2014/0213951 A1 | 7/2014 | Pietrusisnki et al. | |
| 2014/0276265 A1 | 9/2014 | Caires et al. | |
| 2014/0276308 A1 * | 9/2014 | DiAngelo | A61F 5/03 602/19 |
| 2014/0330431 A1 | 11/2014 | Hollander et al. | |
| 2015/0173993 A1 * | 6/2015 | Walsh | A61H 1/024 414/4 |

\* cited by examiner

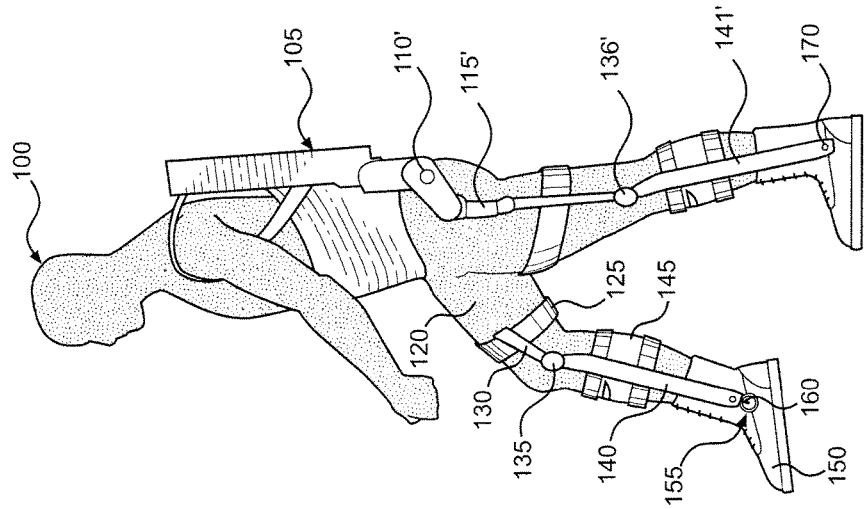
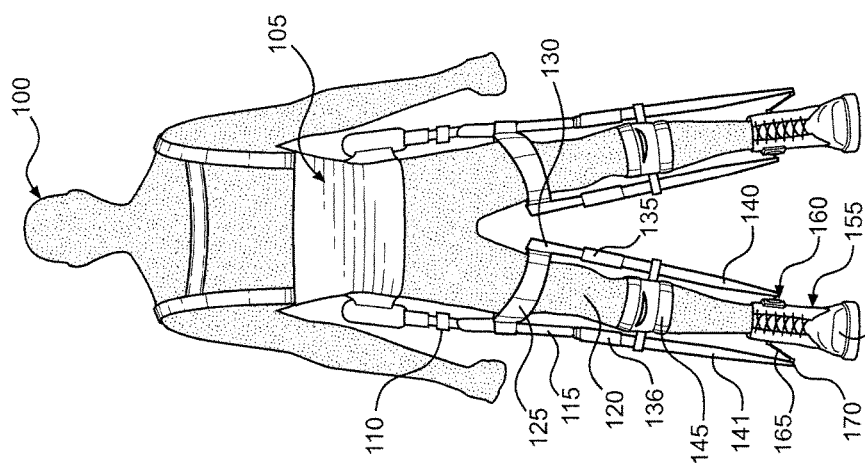

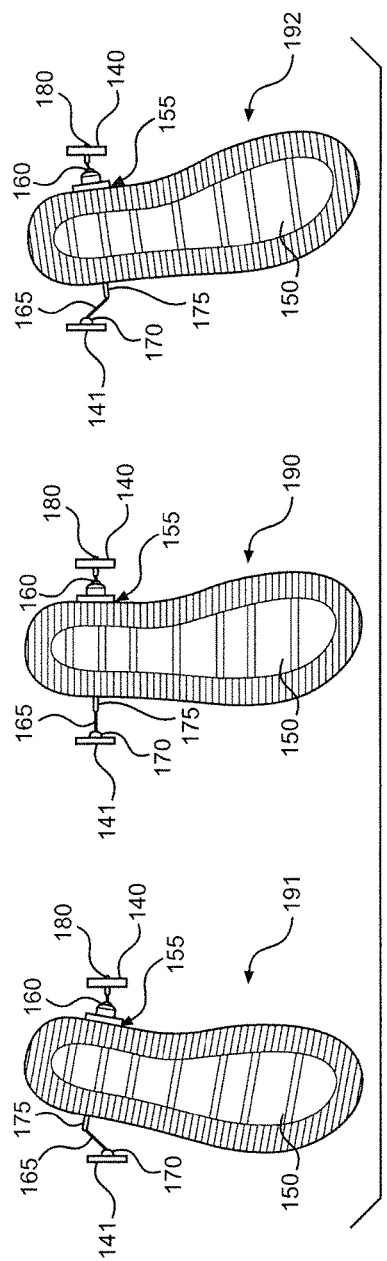
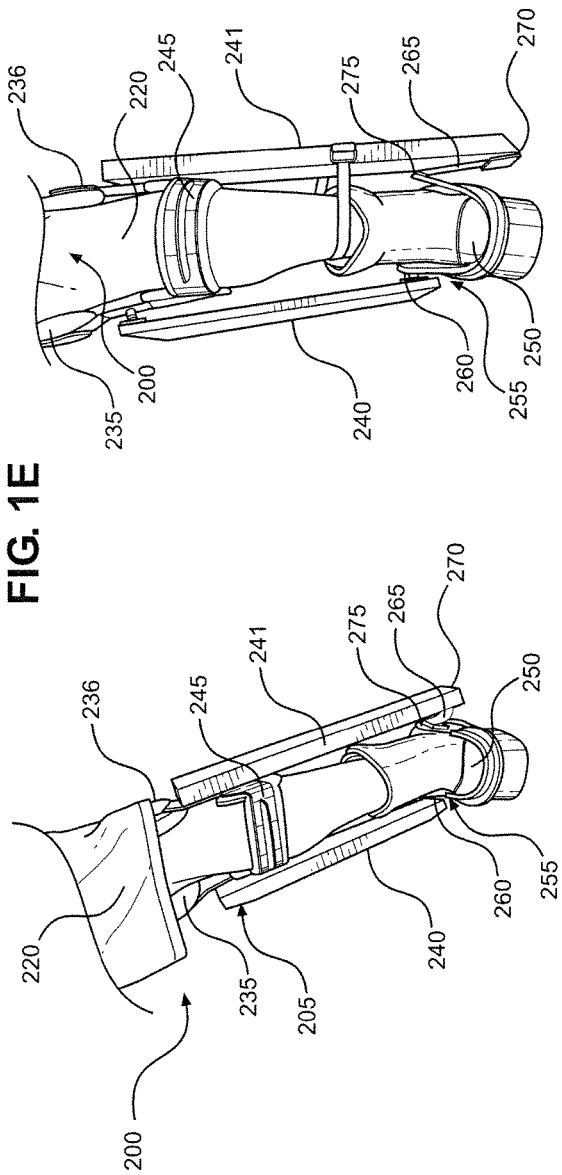

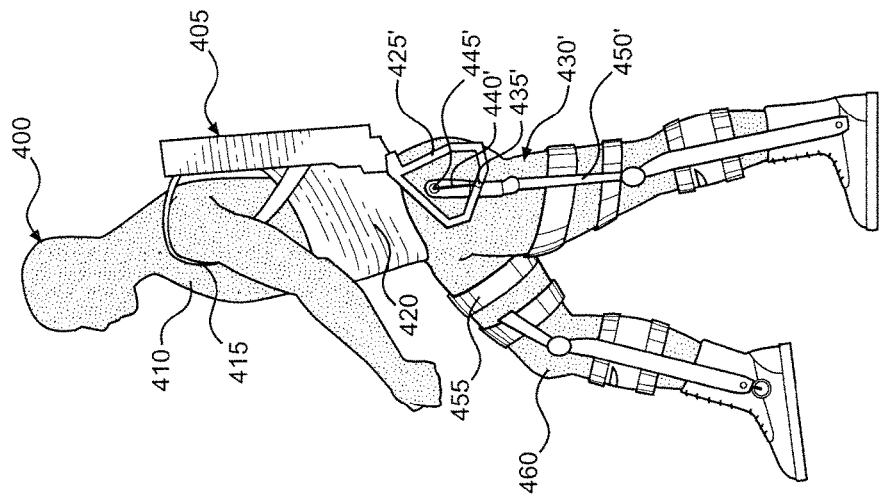
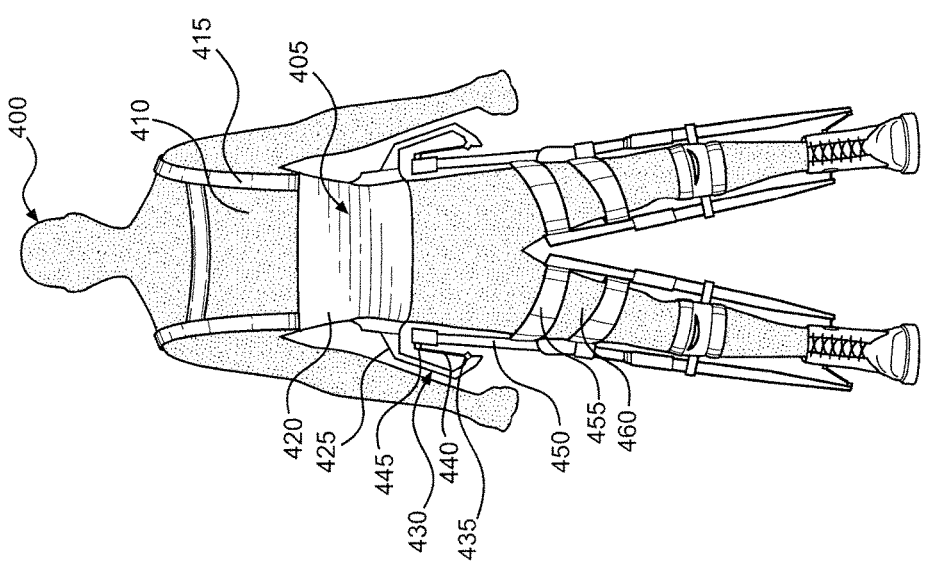

EXOSKELETON AND METHOD OF INCREASING THE FLEXIBILITY OF AN EXOSKELETON JOINT

CROSS REFERENCE TO RELATED APPLICATIONS

This application represents a National Stage application of PCT/US2015/027523 entitled "Exoskeleton and Method of Increasing the Flexibility of an Exoskeleton Joint" filed Apr. 24, 2015, pending, which claims the benefit of U.S. Provisional Patent Application Ser. No. 61/987,696, which was filed on May 2, 2014 and titled "Exoskeleton Joints Incorporating a Tensile Member". The entire content of these applications are incorporated by reference.

GOVERNMENT LICENSE RIGHTS

This invention was made with government support under Contract H92222-14-9-0001 awarded by the United States Special Operations Command. The government has certain rights in the invention.

FIELD OF THE OF THE INVENTION

The present invention relates to a device and method that augments a user's carrying capacity and strength, increasing performance and aiding in the prevention of injury during the execution of certain load-bearing or strength-requiring tasks. More particularly, the present invention relates to a device suitable for use by a person engaging in weight-bearing tasks, the device comprising a set of artificial limbs and related control systems that potentiate improved function of the user's appendages including, but not limited to, greater strength and endurance in the user's legs, allowing for more weight to be carried by the user while walking.

BACKGROUND OF THE INVENTION

Wearable exoskeletons have been designed for medical, commercial and military applications. Medical exoskeletons are designed to help restore a user's mobility. Commercial and military exoskeletons help prevent injury and augment a user's stamina and strength by alleviating loads supported by workers or soldiers during strenuous activities. Exoskeletons designed for use by able-bodied users often act to improve the user's stamina by transferring the weight of a tool or load through the exoskeleton structure and to the ground, thus decreasing the weight borne by the user. For the exoskeleton to transfer this weight to the ground, each exoskeleton support member and exoskeleton joint between the exoskeleton weight and the ground must be able to act as a conduit of this force around the user. This requires a degree of rigidity, seen in the joints of current exoskeletons, that can limit the range of motion of some exoskeleton joints. By limiting the flexibility at these joints, the mobility and maneuverability of the exoskeleton is reduced, thereby limiting the usefulness of the exoskeleton in certain applications.

Current exoskeleton designs rely on inflexible compression members to support the weight of the exoskeleton structure, with the exoskeleton joints being comprised of rotating or pivoting components that connect two rigid members at a fixed distance (the distance being the joint itself) and bear weight through compression. This greatly limits the degrees of freedom of one rigid exoskeleton member relative to the adjoining exoskeleton member. While some exoskeleton joints, such as the knee, require rotation only in a single plane with a fixed distance between the connected rigid members, other joints, such as the hip and ankle, are better served by rotation in two or more planes as well as translation. As one example of the consequences of the limited range of motion of exoskeleton joints, current exoskeleton ankles are incapable of any significant eversion or inversion motion. As a result, the bottom of an exoskeleton foot cannot compensate for a slope in the coronal plane, making current exoskeletons incapable of walking on many types of terrain. As another example, the inability (or reduced ability) of exoskeleton ankle and hip joints to rotate in the transverse plane makes turning a walking or standing exoskeleton difficult.

Due to the limitations imposed on exoskeleton use by the restricted range of motion in exoskeleton joints, there exists a need in the art to develop a device that allows improved flexibility in weight-bearing exoskeleton joints.

SUMMARY OF THE INVENTION

Disclosed herein are devices and methods that allow for greatly improved flexibility in weight-bearing exoskeleton joints. In addition to enhancing the flexibility of exoskeleton joints and allowing for improved exoskeleton mobility under a range of movements and terrain conditions, these devices and methods have additional benefits relating to decreased exoskeleton weight and improved exoskeleton fitting to an exoskeleton user.

In particular, the present invention is directed to an exoskeleton comprising a plurality of interconnected support elements configured to be coupled to body portions of a user. Each of the support elements constitutes a rigid compression member, and at least two of the support elements are interconnected through a tensegrity joint. The joint includes a first tensile member having a first end and a second end. The first end of the first tensile member is coupled to a first support element of the at least two support elements, and the second end is coupled to a second support element of the at least two support elements.

In one embodiment, the joint is an ankle joint, the first support element is a first shank and the second support element is a boot. The first shank is configured to be coupled to a leg of the user with a brace, and the boot is configured to be coupled to a foot of the user. Preferably, the first tensile member is the only connection between the first shank and the boot at the ankle joint. In another embodiment, a second tensile member has a first end coupled to a third support element of the at least two support elements and a second end coupled to the boot. The third support element is a second shank, the second shank configured to be coupled to the leg of the user with the brace.

In still another embodiment, the joint is a hip joint, the first support element is configured to be coupled to a torso of the user and the second support element is configured to be coupled to a leg of the user. The first support element is a torso brace having a hip extension, and the second support element is an upper leg support. The first end of the first tensile member is coupled to the hip extension. Preferably, the first tensile member is the only connection between the hip extension and the upper leg support at the hip joint.

In yet another embodiment, the joint is an abdominal joint, the first support element is configured to be coupled to a torso of the user and the second support element is configured to be coupled to a waist of the user. The first support element is a torso brace having an extension, and the second support element is a waist brace. The first end of the first tensile member is coupled to the extension. Preferably, the first tensile member is the only connection between the extension and the waist brace at the abdominal joint.

Overall, the various embodiments can be used alone or in combination to increase the flexibility of the associated weight-bearing exoskeleton joints. Additional objects, features and advantages of the invention will become more readily apparent from the following detailed description of preferred embodiments thereof when taken in conjunction with the drawings wherein like reference numerals refer to common parts in the several views.

BRIEF DESCRIPTION OF THE DRAWINGS

FIG. 1A is a front view of an exoskeleton constructed in accordance with a primary embodiment of the present invention;

FIG. 1B is a side view of the exoskeleton of the primary embodiment;

FIG. 1E shows the right foot and ankle joint of the primary embodiment in a two-dimensional transverse plane view and demonstrates movement of the ankle joint in lateral and medial rotation relative to the neutral ankle position.

FIG. 2A shows a prototype of the primary embodiment in a first position;

FIG. 2B shows the prototype in a second position;

FIG. 4A is a front view of an exoskeleton constructed in accordance with a third embodiment of the present invention;

FIG. 4B is a side view of the exoskeleton of the third embodiment;

DETAILED DESCRIPTION OF THE PREFERRED EMBODIMENTS

Figure 1C:
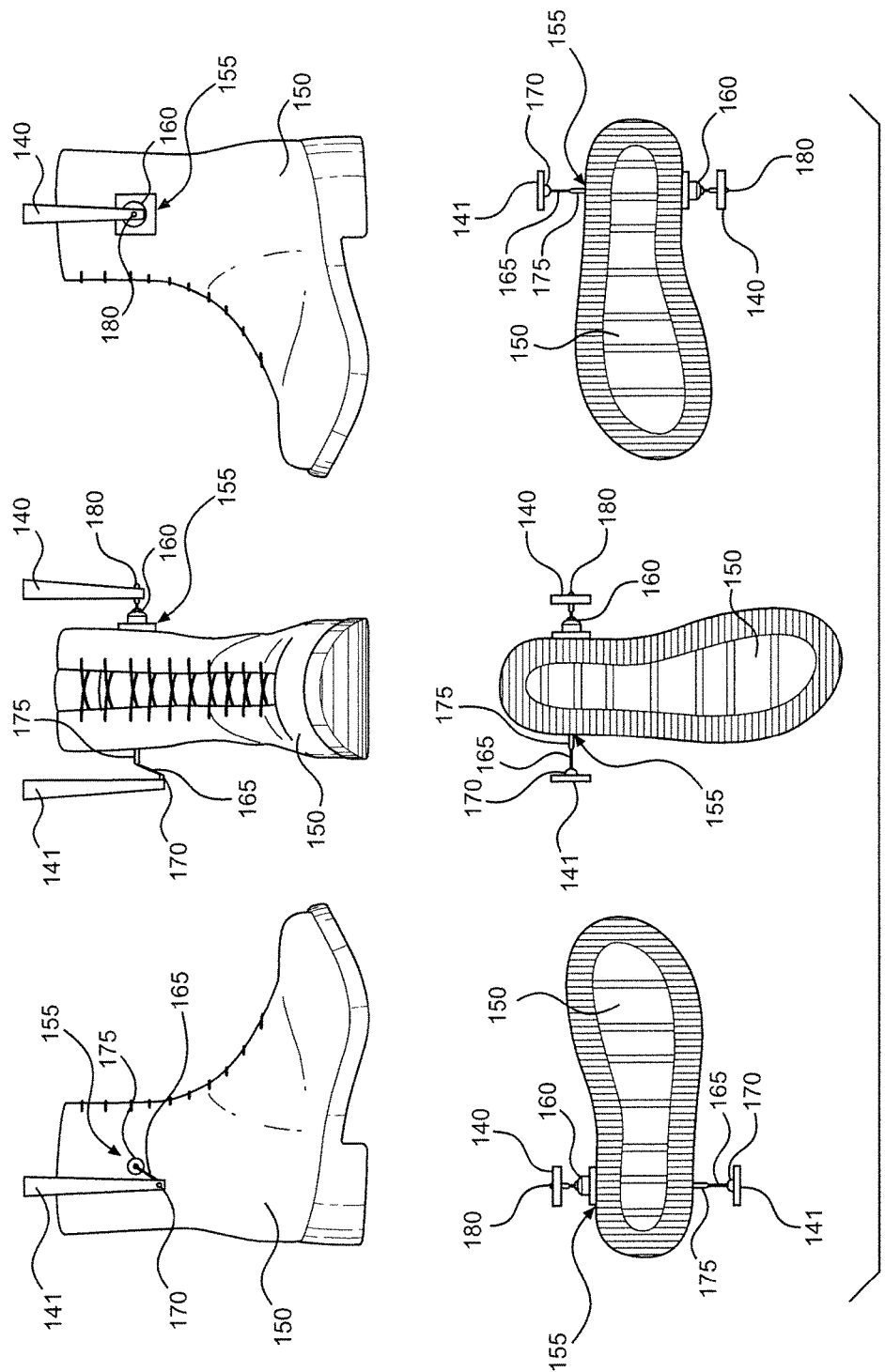
FIG. 1C shows a right foot and ankle joint of the primary embodiment in a neutral ankle position.

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to employ the present invention.

In connection with the present invention, the flexibility of exoskeleton joints are improved by the incorporation of one or more tensile member into an exoskeleton joint. These tensile members act either in tandem with or instead of rotational components of exoskeleton joints to allow a greater degree of freedom and flexibility in the affected joint without compromising the ability of the affected joint to bear weight.

Unlike the design of current exoskeletons, the human skeletal system is comprised of both inflexible compression members (i.e., bones) as well as tensile members (i.e., ligaments and tendons). These tensile members allow a large range of motion at certain joints by enabling small shifts in the positions of compression members relative to each other. This is well demonstrated by the movements of the bones in the human forearm as the wrist is rotated. While the anatomical design of human joints cannot be directly applied to exoskeleton joints, the principle of tensegrity can be applied to exoskeleton joints. For the purposes of the present invention, a tensegrity design is defined as a design that makes use of compression members that are under continuous compression, with these compression member connected (and held in compression) by tensile members that are under continuous tension. Through use of these tensile members in an exoskeleton joint, the number of degrees of freedom within which two joint-connected compression members can move is increased. Specifically, these tensile-linked joints allow linked compression members to shift relative to each other in additional ways compared to the compression member linkages of current exoskeleton joints (current exoskeleton joints being limited to rotational movements between linked compression members). The improved flexibility at these joints not only improves exoskeleton maneuverability under conditions in which exoskeletons are currently used, such as movement upon flat surfaces, but also allows for exoskeleton use in conditions that preclude the use of current exoskeleton designs, such as terrain sloped steeply in the coronal plane.

In addition to improved joint flexibility, the incorporation of tensile members into exoskeletons also has additional advantages. Tensile members in some cases are substantially lighter than their rigid counterparts, as seen in the components of suspension bridges compared to those of steel frame bridges. In the case of exoskeleton joints, tensile components can replace heavier and more expensive machined joint components. Further, the length of a tensile component can be changed relatively easily (either during manufacture or in post-manufacture adjustment), allowing for improved fitting of an exoskeleton to a user without the more complicated or costly modification of rigid components.

The primary embodiment of the present invention comprises an exoskeleton device with a mechanical design that incorporates a tensile member on the inner side of the exoskeleton ankle and a ball-and-socket joint on the outer side of the exoskeleton ankle. The tensile member and ball-and-socket joint couple the lower leg shanks of the exoskeleton to a boot, or similar ground interface device, that can be coupled, in turn, to the exoskeleton user. This mechanical design increases the flexibility of the ankle joint in inversion, eversion and lateral and medial rotational motions, in addition to allowing the plantarflexation and dorsiflexation movements available in current exoskeleton ankle joints. The weight of the exoskeleton is borne by both the ball-and-socket joint and the tensile member since the ball-and-socket joint connects the inner leg shank to the inner side of the boot while the tensile member suspends the outer leg shank and connects it to the outer side of the boot.

In some embodiments, the tensile member is a cable. In another embodiment, the tensile member is a high-strength polymer cord or strap. In some embodiments, the tensile member incorporates a swivel in order to prevent the tensile member from twisting. In other embodiments, the tensile member is a rigid element with rotatable connections to both the boot and the shank. In another embodiment, the tensile member is a series of ball-and-socket joints (e.g., a ball chain). In another embodiment, the relative positions on the ankle of the ball-and-socket and tensile member are transposed. In another embodiment, more than one tensile member connects a single leg shank to the boot device. In another embodiment, a single, flexible tensile member (such as a cable) passes through one point on the shank in such a way as to be able to allow the shank to slide along the length of the tensile member (e.g., through a loose ring at the bottom of the shank), with the tensile member being connected to two points on the boot. In some embodiments, the inner or outer leg shanks are connected to the user's leg in a different manner than that shown in FIGS. 1A-E (described below), using any of the plurality of means known to one skilled in the art of exoskeleton design. In another embodiment, the boot device is designed so as to be easily attached and detached to the exoskeleton shanks at the ankle joint. In another embodiment, the length of the tensile member can be adjusted, either by changing out the tensile member for a tensile member of a different length or by use of a tensile member that has an adjustable length.

A depiction of a primary embodiment is shown in FIGS. 1A-E. With reference to FIGS. 1A and 1B, a user 100 is shown wearing an exoskeleton 105. Exoskeleton 105 is supported by hip joint 110, which is connected to an upper leg support 115. Upper leg support 115 is coupled to a leg 120 of user 100 by a thigh brace 125, which is additionally connected to an inner thigh support 130. Inner thigh support 130 and upper leg support 115 are connected to an inner knee joint 135 and an outer knee joint 136, respectively. Inner knee joint 135 is connected to an inner shank 140, while outer knee joint 136 is connected to an outer shank 141. Both inner shank 140 and outer shank 141 are coupled to leg 120 of user 100 with a calf brace 145. Inner shank 140 is rotatably connected to a boot 150 at an ankle joint 155 by a ball-and-socket joint 160. Outer shank 141 is connected to boot 150 at ankle joint 155 by a tensile member 165 through a tensile-shank coupler 170. Optionally, additional connections between boot 150 of the user and the rigid lower leg (i.e., inner and outer shanks 140 and 141) can be used to limit the motion in one or more axes. For example, a tensile strap between the bottom end of outer shank 141 and boot 150 will effectively limit eversion and reduce the possibility of ankle eversion injuries. As the structure of exoskeleton 105 can take various forms, as is known in the art, the portions of exoskeleton 105 unrelated to the present invention will not be detailed further herein.

Figure 1D:
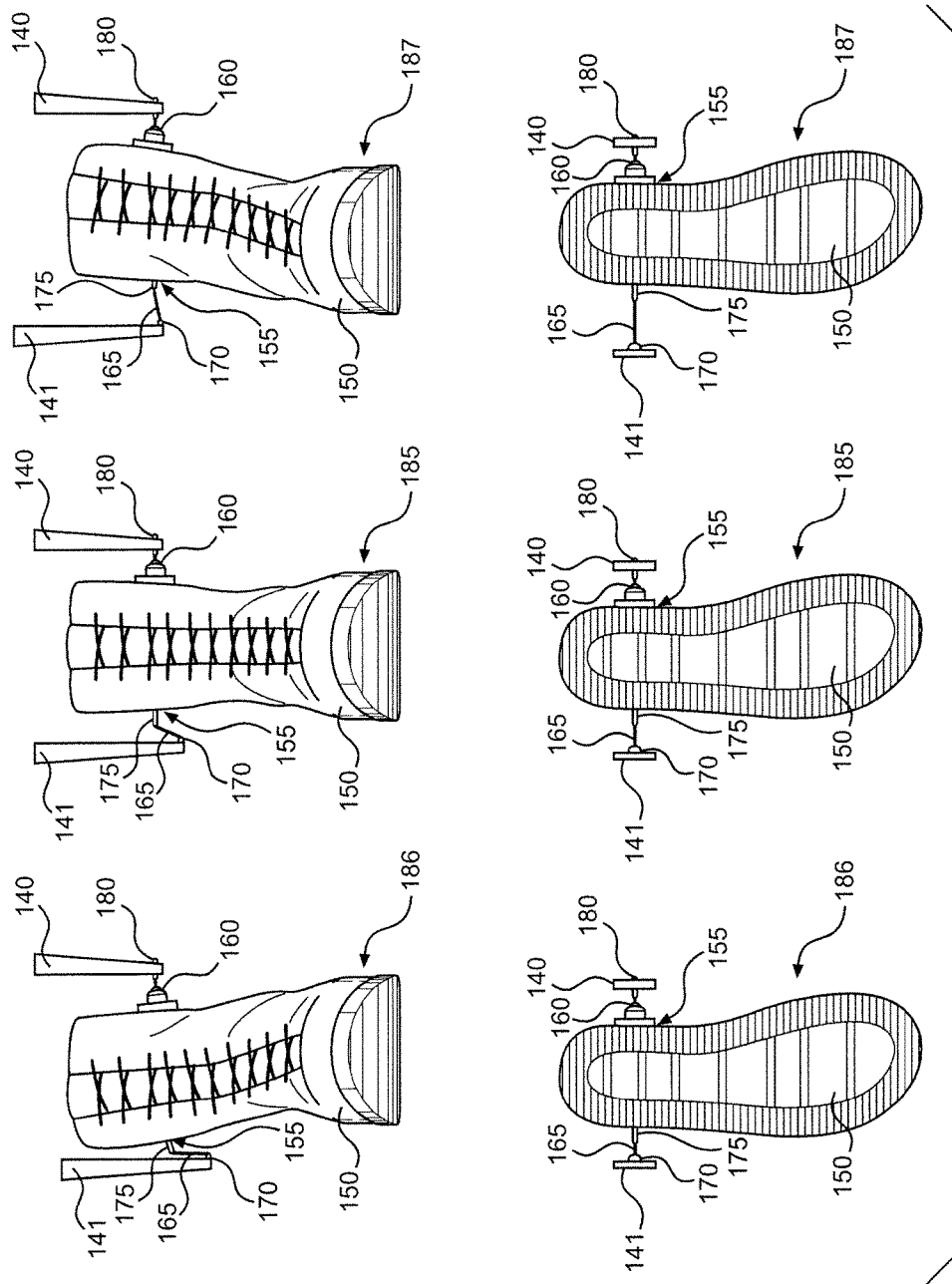
FIG. 1D shows the right foot and ankle joint of the primary embodiment and demonstrates movement of the joint in inversion and eversion relative to the neutral ankle position.

With reference to FIG. 1C, ankle joint 155 and boot 150 are shown in a neutral ankle position from several angles. As discussed above, outer shank 141 is connected to tensile-shank coupler 170, and tensile-shank coupler 170 is connected to tensile member 165. At the other end, tensile member 165 connects to a tensile-boot coupler 175, and tensile-boot coupler 175 is connected to boot 150. Ball-and-socket joint 160 connects inner shank 140 to boot 150 via a bolt 180, which passes through inner shank 140. With reference to FIG. 1D, ankle joint 155 and boot 150 are again shown from multiple angles. A neutral ankle position is illustrated at reference numeral 185, an ankle in eversion is illustrated at reference numeral 186 and the ankle in inversion is illustrated at reference numeral 187. With reference to FIG. 1E, ankle joint 155 and boot 150 are shown in a neutral ankle position at reference numeral 190. At reference numeral 191, the ankle is in a laterally rotated position and, at reference numeral 192, the ankle is in a medially rotated position.

As an example of the primary embodiment, consider an exoskeleton and user walking along a smooth and level surface that is adjoining a sloped surface. If the exoskeleton user wishes to walk along the sloped surface, current exoskeleton ankle designs that do not allow inversion and eversion of the ankle joint would only allow the exoskeleton user to walk directly up or down the sloped surface (i.e., with the slope in the sagittal plane), which may not be the most direct path from the exoskeleton position to a chosen destination. In contrast, the primary embodiment allows the exoskeleton user to walk up the slope, down the slope, along the side of the slope (i.e., with the slope in the coronal plane) or any direction in between, thereby enabling more direct travel to a destination. Further, if one considers the uneven nature of many surfaces, including either natural terrain or terrain with complicated man-made features, the ability of the ankle to evert or invert provides better traction on these surfaces by allowing more of the bottom of the boot to contact the ground. The increased ability to rotate at the ankle further aids navigation over uneven surfaces by making it easier for the user to turn the exoskeleton.

A prototype of the primary embodiment is illustrated in FIGS. 2A and 2B. In general, a prototype exoskeleton 205 is labeled with reference numerals corresponding to those used in FIGS. 1A-E, each reference numeral being incremented by 100. As can be seen in FIGS. 2A and 2B, the use of a tensile member at an ankle joint 255 enables greater freedom of movement for an ankle of user 200 and, hence, for a leg of 220 of user 200.

A second embodiment of the present invention comprises an exoskeleton device with a mechanical design that incorporates more than one tensile member into an ankle joint of the exoskeleton. More specifically, the exoskeleton device incorporates three tensile members into the ankle joint of the exoskeleton, with one tensile member on each of the inner, outer and rear sides of the ankle joint. This mechanical design increases the flexibility of the ankle joint in inversion, eversion and lateral and medial rotational motions, in addition to allowing the plantarflexation and dorsiflexation movements available in current exoskeletons ankle joints. The weight of the exoskeleton is borne by each tensile member: one tensile member suspends the outer leg shank and connects it to the outer side of the boot; a second tensile member suspends the inner leg shank and connects it to the inner side of the boot; and a third tensile member suspends the rear leg shank and connects it to the rear side of the boot.

A depiction of the second embodiment is shown in FIGS. 3A-E. With reference to FIGS. 2A and 2B, a user 300 is shown wearing an exoskeleton 305. Exoskeleton 305 is supported by a hip joint 310, which is connected to an upper leg support 315. Upper leg support 315 is coupled to a leg 320 of user 300 by thigh brace 325, which is additionally connected to an inner thigh support 330. Inner thigh support 330 and upper leg support 315 are connected to an inner knee joint 335 and an outer knee joint 336, respectively. Inner knee joint 335 is connected to an inner shank 340, while outer knee joint 336 is connected to an outer shank 341. Both inner shank 340 and outer shank 341 are coupled to leg 320 of user 300 with a calf brace 345. Inner shank 340 is connected to a boot 350 at an ankle joint 355 by an inner tensile member 360 through an inner tensile-shank coupler 365. Outer shank 341 is connected to boot 350 at ankle joint 355 by an outer tensile member 361 through an outer tensile-shank coupler 366. Although not visible in FIG. 2A, FIG. 2B shows a rear shank 342 connected to boot 350 at ankle joint 355 by a rear tensile member 362 through a rear tensile-shank coupler 367.

Figure 3B:
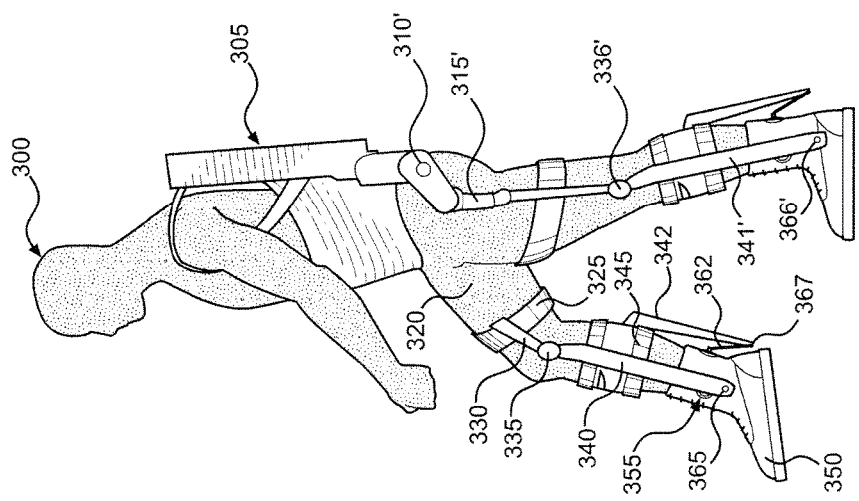
FIG. 3B is a side view of the exoskeleton of the second embodiment.
Figure 3A:
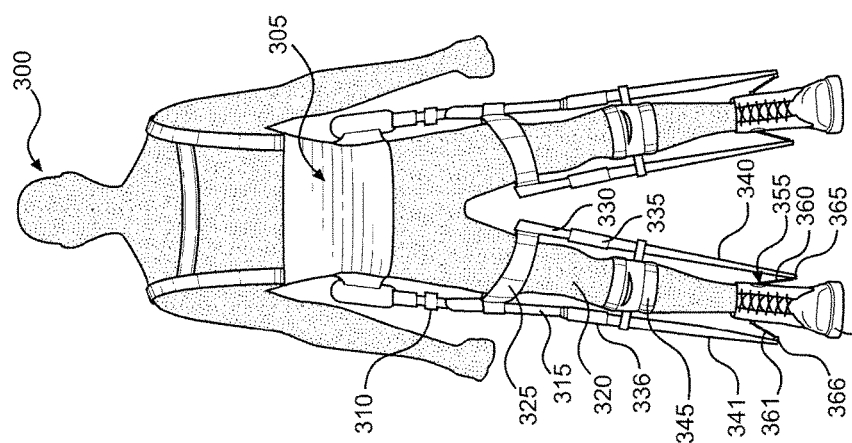
FIG. 3A is a front view of an exoskeleton constructed in accordance with a second embodiment of the present invention.
Figure 3C:
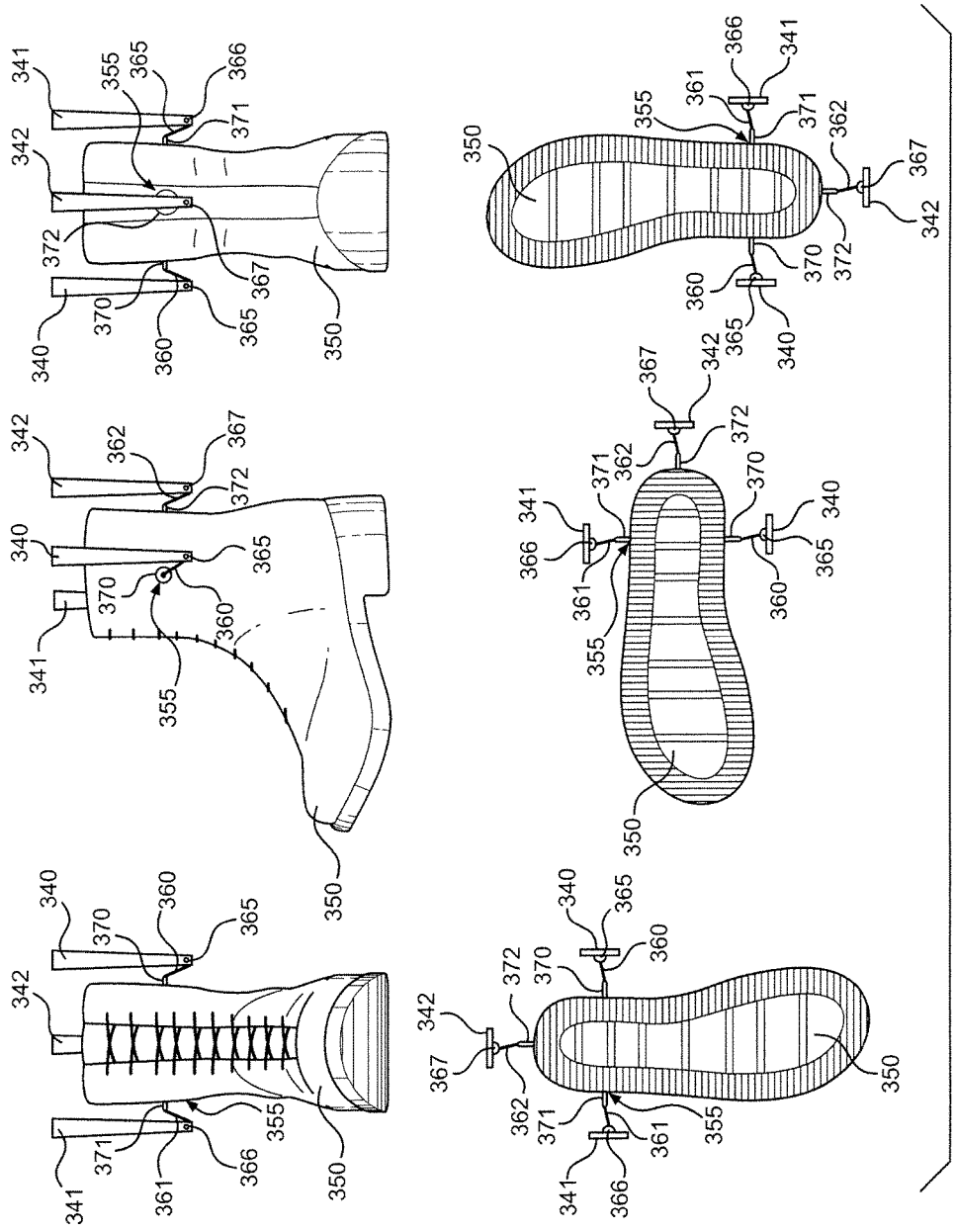
FIG. 3C shows a right foot and ankle joint of the second embodiment in a neutral ankle position.
Figure 3D:
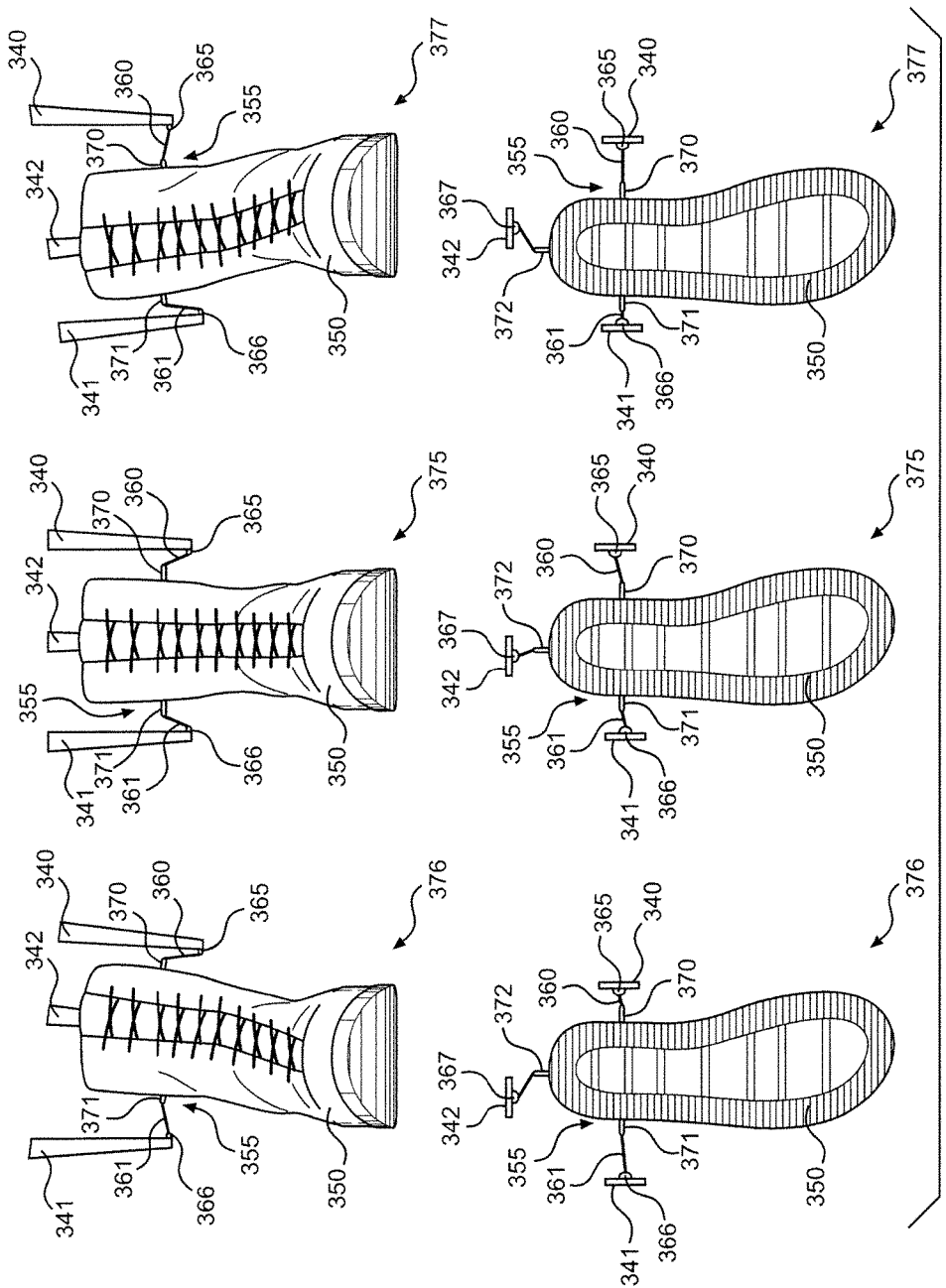
FIG. 3D shows the right foot and ankle joint of the second embodiment and demonstrates movement of the joint in inversion and eversion relative to the neutral ankle position.
Figure 3E:
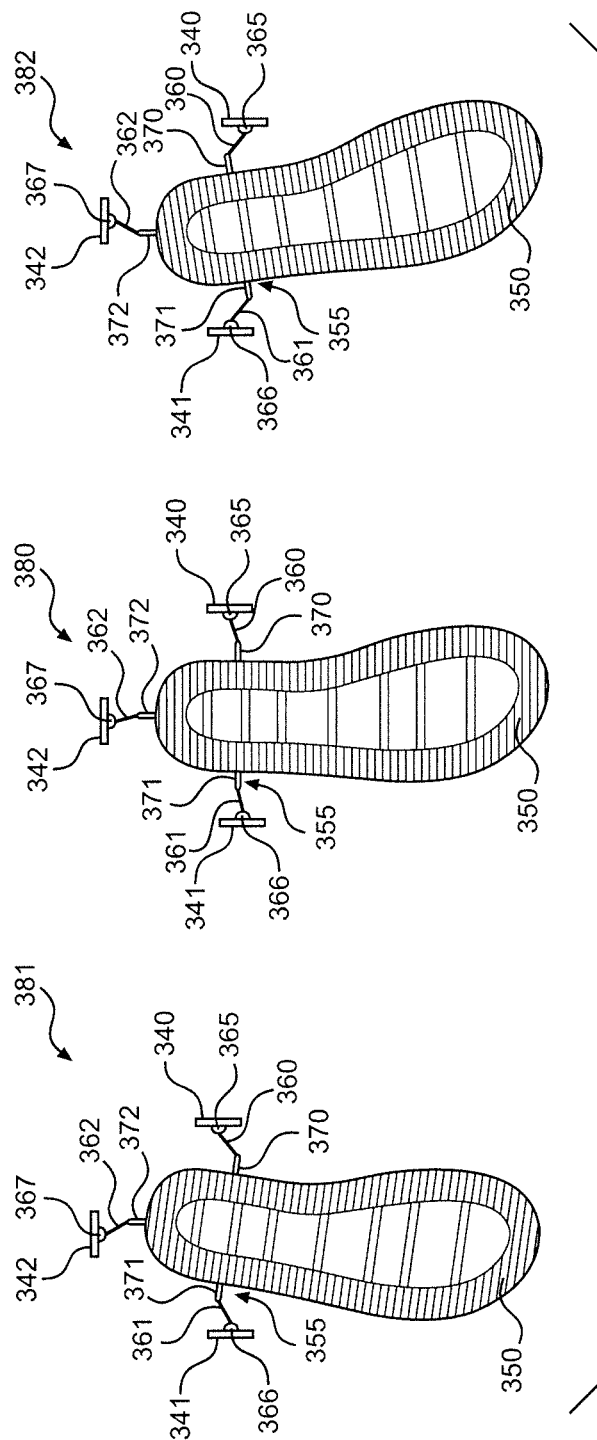
FIG. 3E shows the right foot and ankle joint of the second embodiment in a two-dimensional transverse plane view and demonstrates movement of the ankle joint in lateral and medial rotation relative to the neutral ankle position.

With reference to FIG. 3C, ankle joint 355 and boot 350 are shown in a neutral ankle position from several angles. As discussed above, inner shank 340 is connected to inner tensile-shank coupler 365, and inner tensile-shank coupler 365 is connected to inner tensile member 360. At the other end, inner tensile member 360 connects to an inner tensile-boot coupler 370, and outer tensile-boot coupler 370 is connected to boot 350. Similarly, outer tensile member 361 connects to an outer tensile-boot coupler 371, and outer tensile-boot coupler 371 is connected to boot 350. Rear tensile member 362 connects to a rear tensile-boot coupler 372, and rear tensile-boot coupler 372 is connected to boot 350. With reference to FIG. 3D, ankle joint 355 and boot 350 are again shown from multiple angles. A neutral ankle position is illustrated at reference numeral 375, and ankle in eversion is illustrated at reference numeral 376 and an ankle in inversion is illustrated at reference numeral 377. With reference to FIG. 3E, ankle joint 355 and boot 350 are shown in a neutral ankle position at reference numeral 380. At reference numeral 381, the ankle is in a laterally rotated position, and, at reference numeral 382, the ankle is in a medially rotated position.

As an example of the second embodiment, consider an exoskeleton and user walking along a smooth and level surface that is adjoining a sloped surface. If the exoskeleton user wishes to walk along the sloped surface, current exoskeleton ankle designs that do not allow inversion and eversion of the ankle joint would only allow the exoskeleton user to walk directly up or down the sloped surface (i.e., with the slope in the sagittal plane), which may not be the most direct path from the exoskeleton position to a chosen destination. In contrast, the second embodiment allows the exoskeleton user to walk up the slope, down the slope, along the side of the slope (i.e., with the slope in the coronal plane) or any direction in between, thereby enabling more direct travel to a destination. Further, if one considers the uneven nature of many surfaces, including natural terrain or complicated man-made features, the ability of the ankle to evert or invert provides better traction on these surfaces by allowing more of the bottom of the boot to contact the ground. The increase ability to rotate at the ankle further aids navigation over uneven surfaces by making it easier for the user to turn the exoskeleton.

A third embodiment of the present invention comprises an exoskeleton device with a mechanical design that incorporates a tensile member into a hip joint of the exoskeleton. This mechanical design increases the flexibility of the hip joint in adduction and abduction movements and in lateral and medial rotational motions, in addition to allowing the extension and flexation movements available in prior art exoskeletons hip joints. The weight of the exoskeleton torso is borne by the tensile member, with the tensile member suspending the exoskeleton hip above the leg.

As with the first and second embodiments, in some embodiments, the tensile member is a cable. In some embodiments, the tensile member incorporates a swivel in order to prevent the tensile member twisting. In other embodiments, the tensile member is a rigid element with rotatable connections to both the exoskeleton hip and exoskeleton leg. In another embodiment, the tensile member is a series of ball-and-socket joints (e.g., a ball chain). In some embodiments, the hip is oriented relative to the upper leg in a different what than that shown in FIGS. 4A-D (described below), using any of the plurality of means known to one skilled in the art of exoskeleton design. In another embodiment, the device is designed so as to be easily attached and detached, allowing separation and reattachment of the top of the exoskeleton legs at the hip joints. In another embodiment, the length of one or more tensile member can be adjusted, either by changing out the tensile member for a tensile member of a different length or by use of a tensile member that has adjustable length.

Figure 4C:
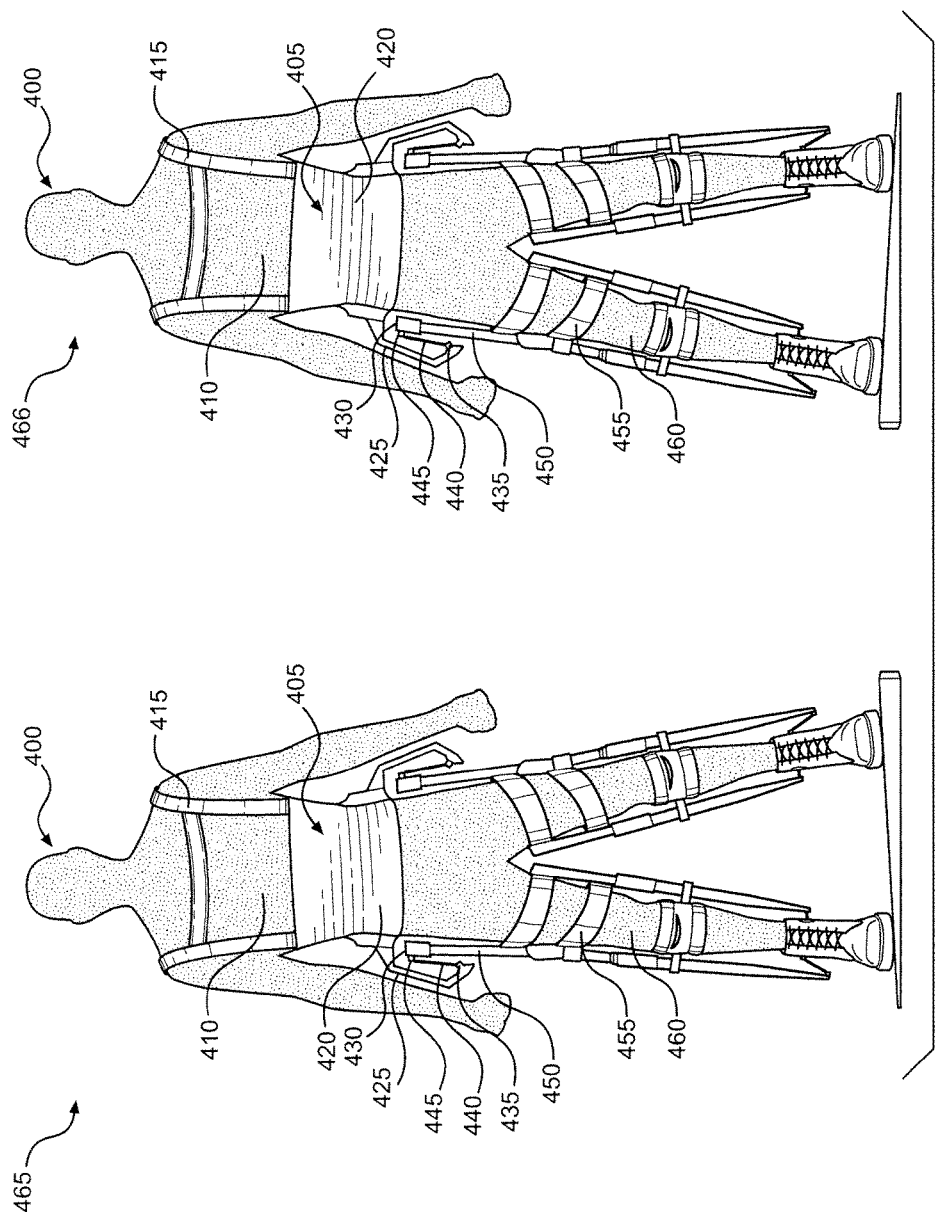
FIG. 4C is a front view of the exoskeleton of the third embodiment demonstrating hip adduction and abduction.

A depiction of the third embodiment is shown in FIGS. 4A-D. With reference to FIGS. 4A and 4B, user 400 is shown wearing an exoskeleton 405. Exoskeleton 405 is coupled to a torso 410 of user 400 by a plurality of straps 415. Exoskeleton 405 is supported by a torso brace 420, which includes an exoskeleton hip extension 425 at an exoskeleton hip joint 430. Exoskeleton hip extension 425 is connected to a hip extension coupler 435, and hip extension coupler 435 is connected to a tensile member 440. Tensile member 440 is connected to a leg coupler 445, which is located at the top of an upper leg support 450. Upper leg support 450 is connected to a plurality of thigh braces 455, and the plurality of thigh braces 455 are coupled to a leg 460 of user 400.

Figure 4D:
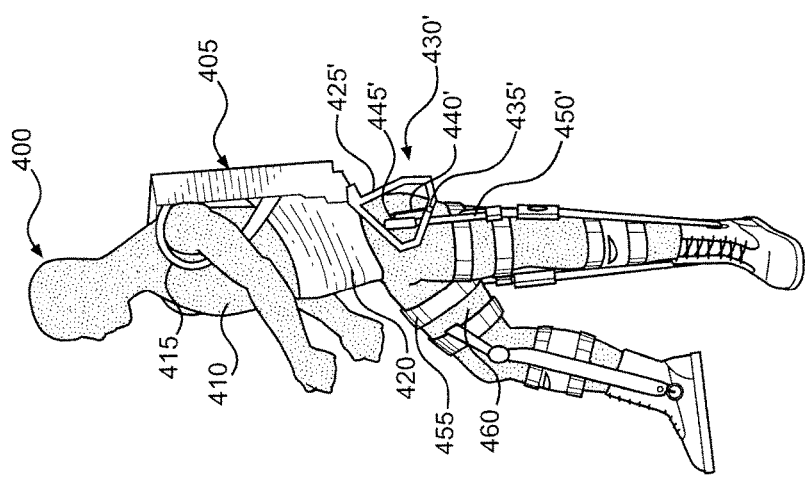
FIG. 4D is a side view of the exoskeleton of the third embodiment demonstrating hip lateral rotation.

With reference to FIG. 4C, exoskeleton 405 is shown on a coronal plane slope with hip joint 430 in two positions. As indicated at reference numeral 465, leg 455 is shown in adduction at hip joint 430, and leg 455' is shown in abduction at hip joint 430'. At reference numeral 466, leg 455' is shown in adduction at hip joint 430', and leg 455 is shown in abduction at hip joint 430. With reference to FIG. 4D, exoskeleton 405 is shown with leg 455' engaging in lateral hip rotation relative to hip joint 430' while leg 455 is lifted. This illustrates the movement that would be executed if user 400 wished to turn to the right.

As an example of the third embodiment, consider a prior art exoskeleton and user standing in a narrow hallway. If the user wanted to turn the exoskeleton around, it would be very difficult since the exoskeleton has little or no ability rotate the hip joint (or any other leg joint) laterally. In contrast, if the exoskeleton were constructed in accordance with the third embodiment, the exoskeleton user would twist a leg at the hip while stepping with the opposite leg, thereby allowing the exoskeleton to turn in a short distance, or even in place, with little or no distance traveled. This sort of movement is not possible with current exoskeleton hip designs.

The major disadvantage of the design of the third embodiment is that actuation across the hip axis becomes more difficult than with a simple hip pivot, as in a classic exoskeleton design. This is because any attempt to create a hip torque in the sagittal plane will generate torques in the frontal and transverse planes as well, resulting in unintended motion. This is not an issue for the first two embodiments presented above because the double inner and outer joints can attenuate such motion (as long as the actuator pulls between the two joints). It is further important to note that the embodiments shown in FIGS. 4A-D will result in the weight of the leg of the exoskeleton being borne by the wearer during the swing phase of the walking cycle (i.e., when the leg is off the ground). However, it is possible to overcome this issue by providing an additional tensile connection that is just barely slack during the stance phase but will bear the weight of the exoskeleton leg during the swing cycle. The choice of whether this strap should be added is based on the weight of the exoskeleton leg and whether this weight is acceptable for the user to bear during swing.

A fourth embodiment of the present invention comprises an exoskeleton device with a mechanical design that incorporates tensile members into the abdominal and lower back portions of an exoskeleton. This mechanical design increases the flexibility of the torso region of the exoskeleton relative the waist/hip region of the exoskeleton. This design allows the exoskeleton torso and exoskeleton user's shoulders to twist, lean or translate relative to the hips, while a joint between the torso and waist continues to support the weight of the torso portion of the exoskeleton and transfer this force to the exoskeleton waist, hips, legs and ultimately to the surface upon which the exoskeleton is standing.

As with the above embodiments, in some embodiments, the tensile members are cables. In some embodiments, the tensile members incorporate a swivel in order to prevent the tensile members from twisting. In other embodiments, the tensile members are rigid elements with rotatable connections to both the waist and torso. In another embodiment, the tensile members are series of ball-and-socket joints (e.g., a ball chain). In some embodiments, the torso is connected to the waist/hip structure in a different what than that shown in FIGS. 5A-D (described below), using any of the plurality of means known to one skilled in the art of exoskeleton design. In another embodiment, the device is designed so as to be easily attached and detached at the joint formed by the tensile members, allowing separation of the torso portion of the exoskeleton from the waist-hip-legs portion of the exoskeleton. In another embodiment, the length of one or more tensile member can be adjusted, either by changing out the tensile member for a tensile member of a different length or by use of a tensile member that has adjustable length.

Figure 5A:
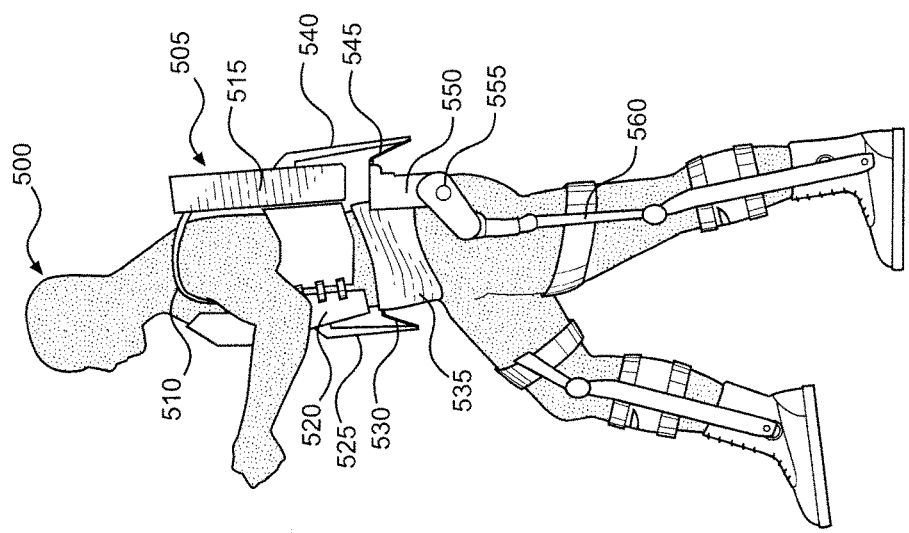
FIG. 5A is a side view of an exoskeleton constructed in accordance with a fourth embodiment of the present invention.
Figure 5B:
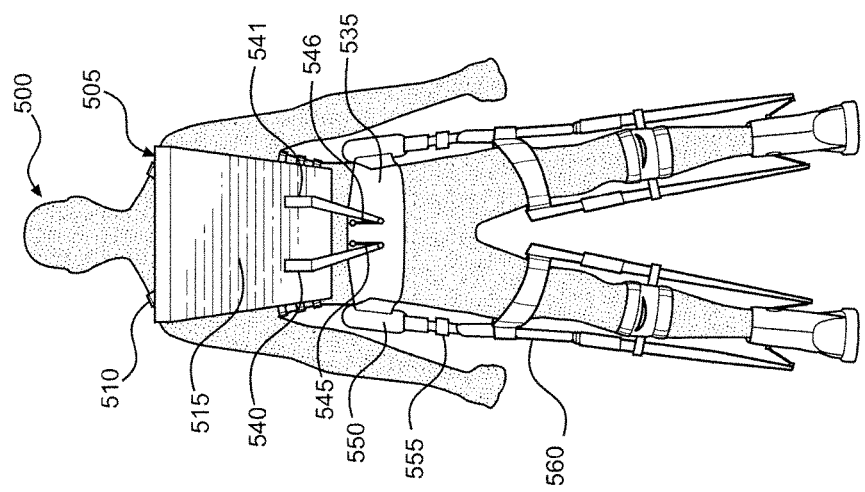
FIG. 5B is a front view of the exoskeleton of the fourth embodiment.
Figure 5C:
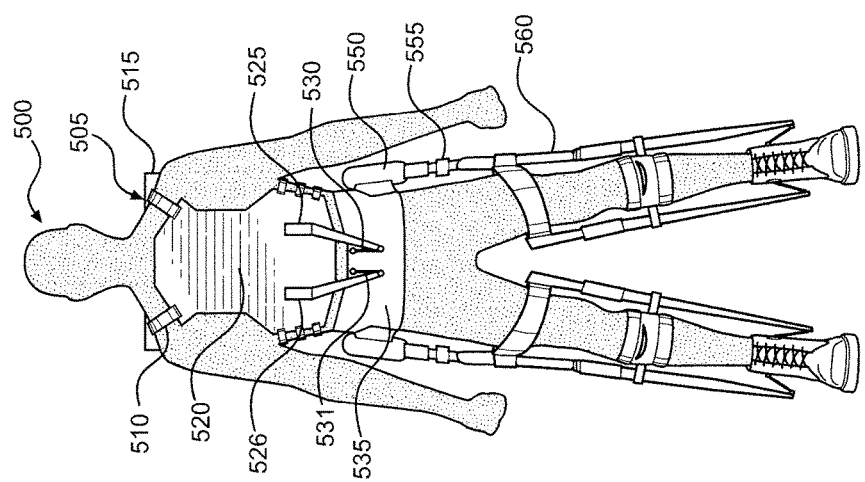
FIG. 5C is a rear view of the exoskeleton of the fourth embodiment.
Figure 5D:
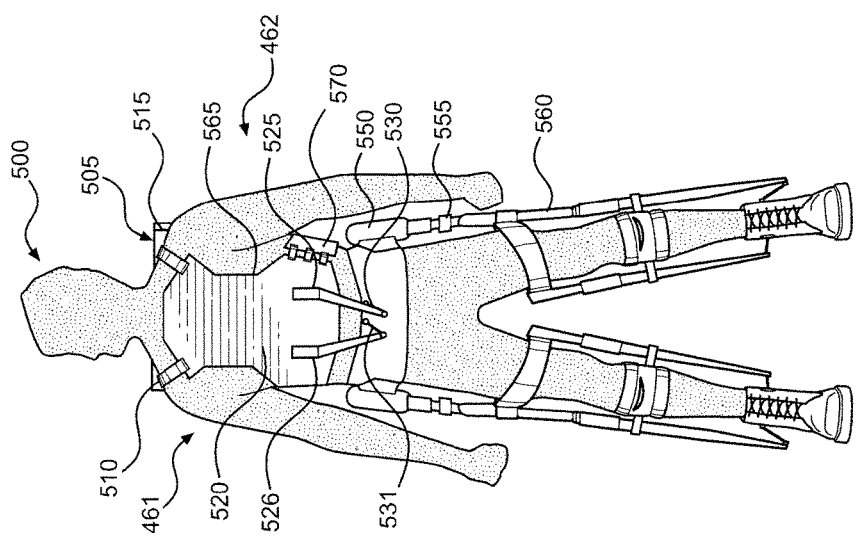
FIG. 5D is a front view of the exoskeleton of the fourth embodiment demonstrating exoskeleton twist at the abdominal joint.

A depiction of the fourth embodiment is shown in FIGS. 5A-D. With reference to FIG. 5A, user 500 is shown wearing an exoskeleton 505. Exoskeleton 505 is coupled to user 500 by a plurality of straps 510, which joins a back portion 515 to a chest plate 520 (thereby defining a torso brace). Chest plate 520 includes a chest extension 525, and chest extension 525 is connected to a front tensile member 530. Front tensile member 530 is connected to a waist brace 535. Back portion 515 includes a back extension 540, which is connected to a rear tensile member 545. Rear tensile member 545 is connected to waist brace 535. A hip support 550 is connected to waist brace 535 and a hip joint 555. Hip joint 555 is connected to a leg support 560. Although not visible in FIG. 5A, FIG. 5B shows a chest extension 526, which is connected to a front tensile member 531. As with front tensile member 530, front tensile member 531 is connected to waist brace 535. Similarly, FIG. 5C shows a back extension 541 connected to a rear tensile member 546. As with rear tensile member 545, rear tensile member 546 is connected to waist brace 535. With reference to FIG. 5D, a torso 565 of user 500 is rotated toward the right (of user 500) about an abdominal tensegrity joint 570.

As an example of the fourth embodiment, consider an exoskeleton being worn by a soldier in a combat environment. As the solder and exoskeleton walk forward with the abdominal joint of the fourth embodiment in a neutral position to facilitate walking, the soldier perhaps spots a potential threat to the left of the soldier. The soldier then rotates both the soldier's torso and the exoskeleton's torso to the left in the transverse plane about the abdominal joint in order to facilitate shouldering a rifle into a firing position. Upon determination that the potential threat is not of continued interest, the soldier then returns his or her torso and the exoskeleton's torso to the neutral position to facilitate walking.

In view of the above, it should be clear that each embodiment of the present invention includes a plurality of interconnected support elements configured to be coupled to body portions of the user, each of the support elements constituting a rigid compression member. At least two of the support elements are interconnected through a tensegrity joint, the joint including a first tensile member having a first end and a second end. The first end is coupled to a first support element of the at least two support elements, and the second end is coupled to a second element of the at least two support elements. In the first embodiment, boot 150 and outer shank 141 are the relevant support elements, and, in the second embodiment, boot 350, inner shank 340, outer shank 341 and rear shank 342 are the relevant support elements. Similarly, in the third embodiment, torso brace 420 and upper leg support 450 are the relevant support elements. In the fourth embodiment, a torso brace, defined by back portion 515 and chest place 520, and waist brace 535 are the relevant support elements. The above-described support elements are connected via tensile members either directly or indirectly (e.g., through extensions of the support elements).

In all embodiments, the tensile-member-containing joint can be configured to: maximize flexibility about the tensile joint; minimize exoskeleton weight; or maximize weight bearing capacity of the exoskeleton. Additionally, in all embodiments, the tensile member can be inelastic or can have some elasticity. Furthermore, in all embodiments, the tensile-member-containing joint can be covered in some way so as to prevent vegetation, clothing or other materials from becoming caught in or interfering with the function of the joint. In all embodiments, the connection support or supports of the tensile member to the exoskeleton can be rigid, incompressible or inflexible, or the connection support or supports can be somewhat compressible or flexible. Finally, in all embodiments, the tensile member can be compressible.

Based on the above, it should be readily apparent that the present invention provides a device and method that enables improved flexibility in weight-bearing exoskeleton joints. Although described with reference to preferred embodiments, it should be readily understood that various changes or modifications could be made to the invention without departing from the spirit thereof.

The invention claimed is:

1. An exoskeleton comprising:
a plurality of interconnected support elements configured to be coupled to body portions of a user, wherein each of the support elements is a rigid compression member, wherein at least two of the support elements are interconnected through a tensegrity joint including a first tensile member held under continuous tension with a first end coupled to a first support element of the at least two support elements and a second end coupled to a second support element of the at least two support elements, and wherein the tensegrity joint is configured such that a weight of the exoskeleton is transferred from the first support element to the second support element through the first tensile member.

2. The exoskeleton of claim 1, wherein:
the tensegrity joint is an ankle joint;
the first support element is a first shank, the first shank configured to be coupled to a leg of the user with a brace; and
the second support element is a boot, the boot configured to be coupled to a foot of the user.

3. The exoskeleton of claim 2, wherein:
the tensegrity joint further includes a second tensile member having a first end and a second end;
the first end of the second tensile member is coupled to a third support element of the at least two support elements;
the second end of the second tensile member is coupled to the boot; and
the third support element is a second shank, the second shank configured to be coupled to the leg of the user with the brace.

4. The exoskeleton of claim 2, wherein the first tensile member is the only connection between the first shank and the boot at the ankle joint.

5. The exoskeleton of claim 1, wherein:
the tensegrity joint is a hip joint;
the first support element is configured to be coupled to a torso of the user; and
the second support element is configured to be coupled to a leg of the user.

6. The exoskeleton of claim 5, wherein:
the first support element is a torso brace having a hip extension, the first end of the first tensile member being coupled to the hip extension; and
the second support element is an upper leg support.

7. The exoskeleton of claim 6, wherein the first tensile member is the only connection between the hip extension and the upper leg support at the hip joint.

8. The exoskeleton of claim 1, wherein:
the tensegrity joint is an abdominal joint;
the first support element is configured to be coupled to a torso of the user; and
the second support element is configured to be coupled to a waist of the user.

9. The exoskeleton of claim 8, wherein:
the first support element is a torso brace having an extension, the first end of the first tensile member being coupled to the extension; and
the second support element is a waist brace.

10. The exoskeleton of claim 9, wherein the first tensile member is the only connection between the extension and the waist brace at the abdominal joint.

11. A method of constructing a joint of an exoskeleton comprising a plurality of interconnected support elements configured to be coupled to body portions of a user, wherein each of the support elements is a rigid compression member, and wherein at least two of the support elements are interconnected through the joint, the method comprising:

configuring the joint as a tensegrity joint by coupling a first end of a first tensile member, which is held under continuous tension, to a first support element of the at least two support elements and coupling the second end of the first tensile member to a second support element of the at least two support elements such that a weight of the exoskeleton is transferred from the first support element to the second support element through the first tensile member.

12. The method of claim 11, wherein the tensegrity joint is an ankle joint, the first support element is a first shank and the second support element is a boot, the method further comprising:
coupling the first shank to a leg of the user with a brace; and
coupling the boot to a foot of the user.

13. The method of claim 12, further comprising:
coupling a first end of a second tensile member to a third support element of the at least two support elements, wherein the third support element is a second shank; and
coupling a second end of the second tensile member to the boot.

14. The method of claim 12, wherein the steps of coupling the first end of the first tensile member to the first shank and coupling the second end of the first tensile member to the boot provide the only connection between the first shank and the boot at the ankle joint.

15. The method of claim 11, wherein the tensegrity joint is a hip joint, the method further comprising:
coupling the first support element to a torso of the user; and
coupling the second support element to a leg of the user.

16. The method of claim 15, wherein:
the first support element is a torso brace having a hip extension;
the second support element is an upper leg support; and
coupling the first end of the first tensile member to the first support element includes coupling the first end to the hip extension.

17. The method of claim 16, wherein the steps of coupling the first end of the first tensile member to the hip extension and coupling the second end of the first tensile member to the upper leg support provide the only connection between the hip extension and the upper leg support at the hip joint.

18. The method of claim 11, wherein the tensegrity joint is an abdominal joint, the method further comprising:
coupling the first support element to a torso of the user; and
coupling the second support element to a waist of the user.

19. The method of claim 18, wherein:
the first support element is a torso brace having an extension;
the second support element is a waist brace; and
coupling the first end of the first tensile member to the first support element includes coupling the first end to the extension.

20. The method of claim 19, wherein the steps of coupling the first end of the first tensile member to the extension and coupling the second end of the first tensile member to the waist brace provide the only connection between the extension and the waist brace at the abdominal joint.

* * * * *